US012805548B1

(12) United States Patent
Fielder et al.

(10) Patent No.: US 12,805,548 B1
(45) Date of Patent: Nov. 24, 2026

(54) DISSOLVABLE BEVERAGE STRIP

(71) Applicant: JRF Technology LLC, Tampa, FL (US)

(72) Inventors: Richard Charles Fielder, Tampa, FL (US); James Milton Rossman, Tampa, FL (US); John Charles Wobensmith, Tampa, FL (US)

(73) Assignee: JRF Technology LLC, Tampa, FL (US)

( * ) Notice: Subject to any disclaimer, the term of this patent is extended or adjusted under 35 U.S.C. 154(b) by 7 days.

(21) Appl. No.: 19/258,749

(22) Filed: Jul. 2, 2025

(51) Int. Cl.

| | |
|---|---|
| ***A61K 47/36*** | (2006.01) |
| ***A23L 2/395*** | (2006.01) |
| ***A23L 2/56*** | (2006.01) |
| ***A23L 2/60*** | (2006.01) |
| ***A23L 2/68*** | (2006.01) |
| ***A61K 9/00*** | (2006.01) |
| ***A61K 9/70*** | (2006.01) |
| ***A61K 31/07*** | (2006.01) |
| ***A61K 31/185*** | (2006.01) |
| ***A61K 31/197*** | (2006.01) |
| ***A61K 31/198*** | (2006.01) |
| ***A61K 31/355*** | (2006.01) |
| ***A61K 31/375*** | (2006.01) |
| ***A61K 31/4045*** | (2006.01) |
| ***A61K 31/4415*** | (2006.01) |
| ***A61K 31/455*** | (2006.01) |
| ***A61K 31/522*** | (2006.01) |
| ***A61K 31/525*** | (2006.01) |
| ***A61K 31/714*** | (2006.01) |
| ***A61K 33/06*** | (2006.01) |
| ***A61K 33/14*** | (2006.01) |
| ***A61K 33/30*** | (2006.01) |
| ***A61K 36/185*** | (2006.01) |
| ***A61K 36/28*** | (2006.01) |
| ***A61K 36/53*** | (2006.01) |
| ***A61K 36/82*** | (2006.01) |
| ***A61K 36/886*** | (2006.01) |
| ***A61K 36/9068*** | (2006.01) |
| ***A61K 47/02*** | (2006.01) |
| ***A61K 47/10*** | (2017.01) |
| ***A61K 47/12*** | (2006.01) |
| ***A61K 47/26*** | (2006.01) |

(Continued)

(52) U.S. Cl.

CPC ................. *A23L 2/395* (2013.01); *A23L 2/56* (2013.01); *A23L 2/60* (2013.01); *A23L 2/68* (2013.01); *A61K 9/0095* (2013.01); *A61K 9/7007* (2013.01); *A61K 31/07* (2013.01); *A61K 31/185* (2013.01); *A61K 31/197* (2013.01); *A61K 31/198* (2013.01); *A61K 31/355* (2013.01); *A61K 31/375* (2013.01); *A61K 31/4045* (2013.01); *A61K 31/4415* (2013.01); *A61K 31/455* (2013.01); *A61K 31/522* (2013.01); *A61K 31/525* (2013.01); *A61K 31/714* (2013.01); *A61K 33/06* (2013.01); *A61K 33/14* (2013.01); *A61K 33/30* (2013.01); *A61K 36/185* (2013.01); *A61K 36/28* (2013.01); *A61K 36/53* (2013.01); *A61K 36/82* (2013.01); *A61K 36/886* (2013.01); *A61K 36/9068* (2013.01); *A61K 47/02* (2013.01); *A61K 47/10* (2013.01); *A61K 47/12* (2013.01); *A61K 47/26* (2013.01); *A61K 47/36* (2013.01); *A61K 47/38* (2013.01); *A61K 47/46* (2013.01)

(58) Field of Classification Search

CPC ... A23L 2/395; A23L 2/56; A23L 2/60; A23L 2/68; A61K 9/0095; A61K 9/7007; A61K 31/07; A61K 31/185; A61K 31/197; A61K 31/198; A61K 31/355; A61K 31/375; A61K 31/4045; A61K 31/4415; A61K 31/455; A61K 31/522; A61K 31/525; A61K 31/714; A61K 33/06; A61K 33/14; A61K 33/30; A61K 36/185; A61K 36/28; A61K 36/53; A61K 36/82; A61K 36/886; A61K 36/9068; A61K 47/02; A61K 47/10; A61K 47/12; A61K 47/26; A61K 47/36; A61K 47/38; A61K 47/46

See application file for complete search history.

(56) References Cited

U.S. PATENT DOCUMENTS

| | | | |
|---|---|---|---|
| 8,048,466 | B2 | 11/2011 | McHugh et al. |
| 9,023,382 | B2 | 5/2015 | Ali et al. |

(Continued)

*Primary Examiner* — Robert A Wax
*Assistant Examiner* — Quanglong N Truong
(74) *Attorney, Agent, or Firm* — Vedder Price P.C.

(57) ABSTRACT

Disclosed and described is a dissolvable beverage strip designed to form a flavored and/or functional beverage and to address the challenges of current systems/formats/methods used with current flavored/functional beverages. The dissolvable beverage strip is formed by spreading an aqueous solution on a substrate to form a uniform layer of solution, followed by drying to remove excess water and creating a dry beverage film, and cutting the dried film to desired dimensions. In various formulations, the solution used to form the dissolvable beverage strip includes water, a water soluble polymer, active ingredients for therapeutic effect, flavor ingredients and sweeteners to enhance taste, fillers and humectants to enhance the overall stability of the final dissolvable beverage strip product, and an emulsifier to facilitate the uniform distribution of ingredients throughout the final dissolvable beverage strip product. This technology provides an effective and convenient alternative to tablets, capsules, powders and flavored ready-to-drink, water-based beverages.

20 Claims, No Drawings

(51) Int. Cl.
*A61K 47/38* (2006.01)
*A61K 47/46* (2006.01)

(56) References Cited

U.S. PATENT DOCUMENTS 9,095,577 B2 8/2015 Myers et al.
9,492,379 B2 11/2016 Park et al.
9,539,334 B2 1/2017 Wood et al.
9,789,112 B2 10/2017 Kohr et al.
9,901,545 B1 2/2018 Fuisz et al.
9,907,759 B2 3/2018 Jeon et al.
10,092,651 B2 10/2018 Jeong et al.
10,925,916 B2 2/2021 Musco et al.
11,179,331 B1 11/2021 Espinoza et al.
11,185,500 B2 11/2021 Maliski et al.
11,331,309 B2 5/2022 Bernardo
11,344,506 B2 5/2022 Bernardo et al.
11,541,002 B2 1/2023 Schobel et al.
11,857,557 B2 1/2024 Espinoza et al.
2004/0247647 A1* 12/2004 Ivory ...................... A23L 27/79 424/440
2005/0019448 A1* 1/2005 Engelhardt ............... A23L 2/56 426/89
2007/0184172 A1* 8/2007 Timmerman ........... A23L 27/79 426/594
2008/0044454 A1* 2/2008 Yang .................... A61K 9/0056 424/443
2008/0075825 A1 3/2008 Fuisz et al.
2014/0333003 A1 11/2014 Allen et al.
2016/0081370 A1* 3/2016 Singer ..................... A23P 10/30 426/282
2017/0290870 A1 10/2017 Schaneville
2019/0336453 A1 11/2019 Kataria et al.
2020/0000773 A1 1/2020 Lee et al.
2020/0101009 A1 4/2020 Schobel et al.
2021/0322306 A1 10/2021 Espinoza et al.
2021/0346385 A1 11/2021 Bains
2022/0023198 A1 1/2022 Espinoza et al.
2022/0047504 A1 2/2022 Davidson et al.
2022/0347117 A1 11/2022 Schobel et al.
2023/0145752 A1 5/2023 Schobel et al.
2023/0149304 A1 5/2023 Schobel et al.
2024/0122908 A1 4/2024 Bernardo
2024/0316026 A1 9/2024 Lu et al.

* cited by examiner

DISSOLVABLE BEVERAGE STRIP

FIELD OF INVENTION

The present invention generally relates to the field of beverage enhancement and, more specifically, to a dissolvable beverage strip.

BACKGROUND

Dietary supplements have become increasingly popular as individuals seek to enhance their health and wellness through additional nutrients they may not receive from their regular diet. These supplements come in various forms, including tablets, capsules, and powders, each offering distinct advantages and disadvantages in terms of convenience, absorption, and efficacy.

One of the challenges associated with traditional dietary supplements, particularly tablets and capsules, is the difficulty some individuals experience in swallowing them. This can be a significant barrier to consistent use, especially for children, the elderly, and those with medical conditions affecting their ability to swallow. Additionally, the absorption rate of nutrients from tablets and capsules can be slower compared to other forms, as they require breakdown in the digestive system before the nutrients become bioavailable. Some tablets are designed to dissolve in water to create a flavored and/or functional beverage; however, the dissolution time for such tablets is lengthy and poses an inconvenience to users.

Powdered dietary supplements that dissolve in water offer an alternative to tablets and capsules. These supplements can be easily mixed with water to create a palatable solution, facilitating easier consumption and potentially faster absorption of nutrients. However, powdered supplements can be messy to handle, often requiring precise measurement and mixing, which can be inconvenient for users. Additionally, powdered supplements are often sold in bulky containers which makes shipping expensive and transporting a smaller, desired amount more difficult. So-called "stick packs" make the transport of smaller quantities of powdered supplements easier; however, stick packs result in high quantities of packaging waste and do little to ameliorate the handling or measuring problems associated with powdered dietary supplements. Further, powdered dietary supplements are particularly sensitive to environmental factors such as moisture.

Additionally, flavored water-based beverages, such as energy drinks, electrolyte replacement drinks, and flavored drinks are popular. Currently, the market for such beverages relies heavily on a beverage bottler or distributor bottling the beverage in a one-time use plastic bottle, often under controlled conditions, such as a hot-fill process, and shipping filled bottles for retail sale. The process has a number of disadvantages. First, the use of one-time use plastic bottles is wasteful. Second, even if the bottles are recyclable, recycling facilities may not be readily available, and adoption of suitable recycling practices remains challenging. Third, single-use plastic bottles, especially those made to withstand hot-fill processes, may be expensive. Fourth, shipping filled plastic bottles is expensive because of their weight.

It would be advantageous to create a beverage solution that addressed the above concerns but still allowed a consumer to experience a flavored drink. Accordingly, a need exists for a more convenient and effective way of creating flavored water-based beverages.

SUMMARY

To address the above and other deficiencies, the present invention contemplates a dissolvable beverage strip and method of manufacturing the same.

The dissolvable beverage strips are formed of a solution comprising a water solvent, water-soluble polymer, and one or more active ingredients. The active ingredients may be varied to achieve different biological effects such as supporting an individual's energy, sleep, immune system, hydration, or general wellness. The solution may also comprise flavor ingredients and sweeteners to enhance taste as well as bulking agents, fillers, and humectants to enhance the overall stability of the final dissolvable beverage strip product, and an emulsifier to facilitate the uniform distribution of ingredients throughout the final dissolvable beverage strip product.

Once the solution is prepared, it can then be cast in a thin film on a carrier surface, dried, and cut into predetermined sizes. The solution may be dried through direct contact with a heated carrier surface or by using hot air impingement or other drying methods as the carrier surface is fed through an oven. Further, the solution may be cast from a casting box, extrusion die, reverse roll coater, or similar solution casting device placed above the carrier surface, and the space between the solution casting device and the carrier surface can be manipulated to adjust the thickness of the film formed by the solution. Once the dissolvable beverage strips have been cut, they can be placed in food-grade foil pouches or similar barrier packaging materials to be protected from degradation caused by oxygen, moisture, or UV exposure.

Dissolvable beverage strips offer several advantages over traditional dietary supplements such as tablets, capsules, and powders. For instance, since dissolvable beverage strips are used to create a beverage solution, they do not pose any problem to those with difficulty swallowing pills. Further, compared to tablets and capsules, it is easier to adjust the dosage of a dissolvable beverage strip by using additional strips, tearing strips into smaller pieces, or simply drinking a desired quantity of the homogenous beverage solution created from the strip. These strips also dissolve at a much faster rate than dissolvable tablets. Further, dissolvable beverage strips require less digestive breakdown than tablets and capsules given that the strip is broken down into its component ingredients in a beverage solution prior to being consumed, thereby increasing the bioavailability of the strips' active ingredients. Additionally, dissolvable beverage strips avoid the messiness and measuring nuisances inherent to powdered supplements. These strips are also easily transported individually, whereas transport of a powdered supplement often requires lugging around a bulky container or finding a smaller container to hold a portion of the powder. Dissolvable beverage strips can further be packaged together in a single container and be used with reusable drinking containers, thereby decreasing shipping costs and packaging waste compared to ready-to-drink beverages and stick packs of powdered supplements. Thus, the present invention significantly improves user experience and efficacy of dietary supplementation.

It is noted that in the present disclosure and particularly in the claims and/or paragraphs, terms such as "comprises," "comprised," "comprising" and the like can have the meaning attributed to them in U.S. patent law; e.g., they can mean "includes," "included," "including," and the like.

These and other embodiments are disclosed or are obvious from and encompassed by the following Detailed Description.

DETAILED DESCRIPTION

For the purposes of promoting and understanding the principles disclosed herein, reference is now made to preferred embodiments and specific language is used to describe the same. It is nevertheless understood that no limitation of the scope of the invention is hereby intended. Such alterations and further modifications of the present disclosure and such further applications of the principles disclosed herein are contemplated as would normally occur to one of skill in the art to which this disclosure relates.

The present invention relates to a dissolvable beverage strip. These strips are designed to flavor beverages and provide a convenient and effective means of delivering nutrients and active ingredients to support various health functions, such as energy, immunity, sleep, hydration, and general wellness support. The strips are typically manufactured as thin sheets with a width of about 2 inches, a length of about 3.5 inches, a thickness of about 6.5 to about 15 mils, and weight of about 0.5 to about 2 grams.

These dissolvable beverage strips also have a dissolution time of less than or equal to 2 minutes in 8 to 16 ounces of water at a temperature of 10° C. This dissolution time can be obtained by first confirming the weight and dimensions of a dissolvable beverage strip sample using an analytical scale and micrometer, respectively. Once these measurements are obtained, one can then remove the cap from a water bottle and fill it with about 16 fluid ounces (500 mL) of water at a temperature of 10° C. The temperature of the water can be confirmed and recorded using a thermometer. Next, the dissolvable beverage strip sample can be loosely rolled into a tube shape and placed through the opening of the bottle. Once the sample is placed in the bottle, a timer is started and the cap is replaced on the bottle. After 30 seconds, the bottle is shaken as needed to facilitate dissolution. Once the strip is completely dissolved (i.e., no particles of the strip are floating in the bottle), the timer is stopped. This time measurement represents the dissolution time of the dissolvable beverage strip. Other similar methods for testing the dissolution rate of a dissolvable beverage strip are generally known to persons of ordinary skill in the art.

The dissolvable beverage strip typically has a tensile strength from about 513.9 MPa to about 3268.3 MPa, with an average tensile strength of about 2358.0 MPa. Further, the dissolvable beverage strip typically has a Young's Modulus from about 10.79 MPa to about 67.60 MPa and an Elongation at break from about 4.29% to about 9.24%, averaging about 43.51 MPa and 6.28%, respectively. These measurements can be obtained by using general principles for determining the tensile properties of plastic and plastic composites, such as those provided by the International Organization for Standardization ("ISO") in ISO 527-1:2019 entitled *Plastics-Determination of Tensile Properties*.

The dissolvable beverage strip is formed from a solution comprising a water solvent, a water-soluble polymer, and one or more active ingredients. The water-soluble polymer may be selected from the group consisting of pullulan, hydroxypropyl methyl cellulose, hydroxyethyl cellulose, hydroxypropyl cellulose, polyvinyl pyrrolidone, carboxymethyl cellulose, polyvinyl alcohol, sodium alginate, polyethylene glycol, tragacanth gum, guar gum, acacia gum, arabic gum, polyacrylic acid, methylmethacrylate copolymer, carboxyvinyl polymer, amylose, high amylose starch, hydroxypropylated high amylose starch, dextrin, pectin, chitin, chitosan, levan, elsinan, collagen, gelatin, zein, gluten, soy protein isolate, whey protein isolate, casein and mixtures thereof. The final dissolvable beverage strip product typically comprises the water-soluble polymer at about 0.1% to about 50% by weight and, more preferably, at about 0.5% to about 40% by weight.

In other embodiments, the solution used to form the dissolvable beverage strip may further comprise flavor ingredients and sweeteners to enhance taste. The final dissolvable beverage strip product typically comprises the flavor ingredients and/or sweeteners at about 0.01% to about 50% by weight and, more preferably, at about 0.05% to about 40% by weight. The flavor ingredients may be naturally derived or artificially synthesized. Potential flavor ingredients include licorice, chamomile, menthol, aniseed, cinnamon, wintergreen, cherry, berry, peach, apple, bourbon, scotch, whiskey, spearmint, peppermint, lavender, cardamon, nutmeg, vanilla, lemon oil, orange oil, ginger, anise, coriander, or coffee. Potential sweeteners include those known to persons of ordinary skill in the art such as sucralose, stevia extract, aspartame, glucose, fructose, sucrose, or flavor-masking agents and bitterness receptor site blockers.

To further enhance flavor, some embodiments of the dissolvable beverage strip will be formed from a solution including one or more acidulants such as citric acid, malic acid, tartaric acid, or phosphoric acid. Such acidulants enhance the flavor of the beverage created using a dissolvable beverage strip by lowering the pH thereof and creating sour flavor notes. The final dissolvable beverage strip product typically comprises these acidulants each at about 0.1% to about 25% by weight and, more preferably, at about 0.5% to about 20% by weight.

In certain embodiments, the solution used to form the dissolvable beverage strip may also include humectants and fillers. The humectants enhance the softness and flexibility of the final dissolvable strip product to aid in handling during converting and packaging. Similarly, the fillers improve the physical handling of the final dissolvable beverage strip product by providing dimensional stability or by absorbing/immobilizing liquid ingredients (including water), humectants, and plasticizers. The humectants and fillers also increase the dissolution rate of the dissolvable beverage strip in water. The final dissolvable beverage strip product typically comprises the one or more fillers each at about 0.01% to about 50% by weight and the humectant at about 0.5% to about 10% by weight. More preferably, the final dissolvable beverage strip product typically comprises the one or more fillers each at about 0.05% to about 40% by weight and the humectant at about 1% to about 5% by weight. Possible humectants include glycerin, di-glycerin, propylene glycol, polyethylene glycol, sorbitol, mannitol, ethoxylated monoglyceride, ethoxylated di-glyceride, and triacetin. Possible fillers include soluble fibers (e.g., corn fiber), insoluble fibers (e.g., oat fiber), cellulose, sugars (e.g., lactose, dextrose, cane sugar, etc.), starches (e.g., tapioca starch), polyhydric alcohols (e.g., mannitol), inorganic material (e.g., calcium carbonate, calcium phosphate, talc, etc.), lubricants (e.g., lecithin), waxes (e.g., propylene glycol monostearate), and dyestuffs (either in soluble form or as pigments).

Some embodiments of the present invention may be formed of a solution that comprises an emulsifier to facilitate the uniform distribution of ingredients throughout the final dissolvable beverage strip product. The final dissolvable beverage strip product typically comprises an emulsifier at about 0.1% to about 10% by weight and, more preferably, at about 0.5% to about 5% by weight. Possible emulsifiers include lecithin (e.g., soy lecithin or sunflower lecithin), mono and di-glycerides of fatty acids, sorbitan esters, sucrose esters of fatty acids, propylene glycol esters of fatty acids and, more preferably, polysorbates (e.g., Polysorbate 60 or Polysorbate 80).

The active ingredients of the solution can be varied depending on the desired effect of the dissolvable beverage strip. Example formulations of solutions used to form dissolvable beverage strips for energy support, sleep support, immune support, hydration support, and general wellness are included in the tables below.

An exemplary embodiment of a dissolvable beverage strip for energy support is shown below in Table 1.

TABLE 1

| Function | Ingredient | Weight % in Dissolvable Beverage Strip |
|---|---|---|
| Solvent | Purified Water | 5.59 |
| Filler | Oat Fiber | 24.17 |
| Polymer | Organic Pullulan | 17.71 |
| Active Ingredient | Taurine | 11.20 |
| Acidulant | Phosphoric Acid (85%) | 9.48 |
| Active Ingredient | Green Tea Caffeine (98%) | 8.89 |
| Flavor Ingredient | Natural Energy Type Flavor | 6.59 |
| Humectant | Glycerin | 4.94 |
| Acidulant | Malic Acid | 4.66 |
| Sweetener | Sucralose | 4.17 |
| Active Ingredient | Niacin (B3), Pantothenic Acid (B5), Pyridoxine HCl (B6), Riboflavin (B2), Methylcobalamin (B12) | 2.60048 |

In the energy support formulation of the dissolvable beverage strip embodied in Table 1, the active ingredients comprise a stimulant, an amino acid, and vitamins. The stimulant is caffeine and the amino acid is taurine. The vitamins include niacin, pantothenic acid, pyridoxine HCl, riboflavin, and methylcobalamin. Further, this formulation weighs about 1150 milligrams and has solubility of less than or equal to 2 minutes in 8 to 16 ounces of water at a temperature of 10° C.

An exemplary embodiment of a dissolvable beverage strip for sleep support is shown below in Table 2.

TABLE 2

| Function | Ingredient | Weight % in Dissolvable Beverage Strip |
|---|---|---|
| Solvent | Purified Water | 9.19 |
| Polymer | Organic Pullulan | 20.6 |
| Flavor Ingredient | Natural Raspberry Lemonade Flavor | 12.34 |
| Active Ingredient | Theanine | 12.24 |
| Acidulant | Malic Acid | 11.31 |
| Filler | Oat Fiber | 8.25 |
| Active Ingredient | Chamomile Extract (20:1) | 5.84 |
| Active Ingredient | Lemon Balm Extract (10:1) | 5.84 |
| Active Ingredient | Passion Flower Extract (10:1) | 5.84 |
| Sweetener | Sucralose | 2.78 |
| Filler | Tapioca Starch | 2.37 |
| Humectant | Glycerin | 1.76 |

TABLE 2-continued

| Function | Ingredient | Weight % in Dissolvable Beverage Strip |
|---|---|---|
| Emulsifier | Polysorbate 80 | 1.26 |
| Active Ingredient | Melatonin | 0.37 |

In the sleep support formulation of the dissolvable beverage strip embodied in Table 2, the active ingredients comprise a variety of sleep enhancers. These sleep enhancers include theanine, chamomile extract, lemon balm extract, passion flower extract, and melatonin. Further, this formulation weighs about 900 milligrams and has a solubility of less than or equal to 2 minutes in 8 to 16 ounces of water at a temperature of 10° C.

An exemplary embodiment of a dissolvable beverage strip for immune support is shown below in Table 3.

TABLE 3

| Function | Ingredient | Weight % in Dissolvable Beverage Strip |
|---|---|---|
| Solvent | Purified Water | 7.41 |
| Polymer | Organic Pullulan | 20.42 |
| Filler | Oat Fiber | 16.70 |
| Active Ingredient | Sodium Ascorbate (88.9%) | 5.84 |
| Flavor Ingredient | Natural Tropical Punch Flavor | 1.19 |
| Acidulant | Malic Acid | 0.75 |
| Filler | Tapioca Starch | 0.12 |
| Active Ingredient | Magnesium Glycinate (20%) | 15.41 |
| Flavor Ingredient | TITAN SWEET ™ | 5.40 |
| Emulsifier | Polysorbate 80 | 0.78 |
| Active Ingredient | Ginger Root PE (4:1), Zinc Bisglycinate (30%), Vitamin E DL-a-Tocopherol (50%), Vitamin A Acetate (500M IU/g) | 14.72 |
| Flavor Ingredient | Natural Smoothenol + Modifiers Liquid Flavor | 9.39 |
| Sweetener | Stevia Extract RA-97 | 1.52 |
| Color | Beet Root Powder PWS 50 462010 | 0.35 |

In the immune support formulation of the dissolvable beverage strip embodied in Table 3, the active ingredients comprise vitamins and antioxidants. The vitamins and antioxidants include sodium ascorbate, magnesium glycinate, ginger root PE, zinc bisglycinate, vitamin E dl-a-tocopherol, and vitamin A acetate. Further, this formulation weighs about 950 milligrams and has a solubility of less than or equal to 2 minutes in 8 to 16 ounces of water at a temperature of 10° C.

An exemplary embodiment of a dissolvable beverage strip for hydration support is shown below in Table 4.

TABLE 4

| Function | Ingredient | Weight % in Dissolvable Beverage Strip |
|---|---|---|
| Solvent | Purified Water | 5.52 |
| Polymer | Pullulan | 20.78 |
| Filler | Oat Fiber | 13.56 |
| Active Ingredient | Potassium Chloride | 11.52 |
| Active Ingredient | Sodium Chloride | 11.22 |
| Active Ingredient | Magnesium Citrate (17%) | 7.87 |
| Flavor Ingredient | Natural Wildberry Flavor | 7.53 |
| Acidulant | Phosphoric Acid (85%) | 7.53 |

TABLE 4-continued

| Function | Ingredient | Weight % in Dissolvable Beverage Strip |
|---|---|---|
| Sweetener | Stevia RA-97 | 3.99 |
| Active Ingredient | Calcium Chloride | 2.45 |
| Flavor Ingredient | Natural Sour Grape Flavor | 2.26 |
| Color | Natural Blue Powder | 1.64 |
| Emulsifier | Sorbitan Monostearate | 0.98 |
| Polymer | Sodium Alginate | 0.9 |
| Polymer | Gum Arabic | 0.9 |
| Flavor Ingredient | Natural Smoothenol + Modifiers Liquid Flavor | 0.49 |
| Active Ingredient | Ascorbic Acid, Niacin (B3), Zinc Oxide (80%), Pyridoxine HCl (B6), Methylcobalamin (B12) | 0.85005 |

In the hydration support formulation of the dissolvable beverage strip embodied in Table 4, the active ingredients comprise electrolyte replacements and vitamins. The electrolyte replacements include potassium chloride, sodium chloride, magnesium citrate, calcium chloride, and zinc oxide. The vitamins include ascorbic acid, niacin, pyridoxine HCl, and methylcobalamin. Further, this formulation weighs about 1500 milligrams and has a solubility of less than or equal to 2 minutes in 8 to 16 ounces of water at a temperature of 10° C.

An exemplary embodiment of a dissolvable beverage strip for general wellness is shown below in Table 5.

TABLE 5

| Function | Ingredient | Weight % in Dissolvable Beverage Strip |
|---|---|---|
| Solvent | Purified Water | 8.06 |
| Flavor Ingredient | Natural Citrus Flavor | 21.23 |
| Acidulant | Malic Acid | 18.20 |
| Filler | Oat Fiber | 17.85 |
| Polymer | Hydroxypropyl Methyl Cellulose (5 cps) | 9.53 |
| Polymer | Hydroxypropyl Methyl Cellulose (15 cps) | 9.53 |
| Active Ingredient | Aloe Extract, Chamomile Extract | 9.54 |
| Sweetener | Sucralose | 6.07 |

In the general wellness formulation of the dissolvable beverage strip embodied in Table 5, the active ingredients comprise botanical ingredients (aloe extract and chamomile extract). Further, this formulation weighs about 800 milligrams and has a solubility of less than or equal to 2 minutes in 8 to 16 ounces of water at a temperature of 10° C.

The above embodiments are exemplary and include one or more ingredients to provide a therapeutic effect. Potential active ingredients and application areas of the dissolvable beverage strip further include, but are not limited to, a probiotic enzyme (e.g., *Bacillus subtilis*) for improving gut health, a prebiotic (e.g., soluble corn fiber) for digestive health, a botanical ingredient (e.g., *Panax ginseng*) for cognitive enhancement, an adaptogen (e.g., Reishi mushroom) for stress relief, or a protein (e.g., hydrolyzed collagen) for joint support. However, flavored beverage strips with no therapeutic agents, for example, solely to make a flavored beverage for recreational enjoyment, are also contemplated and within the scope of the present invention.

Once the solution has been prepared, the dissolvable beverage strip can be manufactured by casting the solution in a thin film on a carrier surface, drying the film to remove excess water, and cutting the dried film into a strip of a predetermined size. The resulting dissolvable beverage strip can then be dissolved in water, thereby releasing its active ingredients for convenient consumption. Further, a user may tear the dissolvable beverage strip into smaller pieces, use additional strips, or change the amount of water used for dissolution to adjust the dosage and/or potency of the resulting beverage.

In some embodiments of the manufacturing process, the carrier surface is a polyester film, such as mylar, or a continuous stainless steel belt. Some embodiments of the manufacturing process may also dry the solution using hot air impingement or other drying methods as the carrier surface is fed through an oven. The carrier surface may also itself be heated, thereby drying the solution through direct contact.

In further embodiments of the manufacturing process, the solution may be cast from a casting box, extrusion die, reverse roll coater, or similar coating device placed above the carrier surface. The space between the casting device and the carrier surface can then be manipulated to adjust the thickness of the film formed by the solution.

Once the film formed by the solution has been dried, it can be wound into a coil or cut into predetermined sizes right away. If polyester film was used as the carrier surface, the film formed by the solution and the polyester film will be joined after drying, requiring separation which can be accomplished using specialized machinery known to persons of ordinary skill in the art.

Once the dissolvable beverage strip is manufactured, it can be packaged in food-grade foil pouches or similar protective packaging materials to protect the dissolvable beverage strip from being degraded by exposure to oxygen, moisture, or UV light. Pieces of parchment paper may also be placed between dissolvable beverage strips which are packaged in the same protective materials so as to prevent adhesion between them.

What is claimed:

1. A dissolvable beverage strip comprising:

a water-soluble polymer, wherein the water-soluble polymer is one or more of pullulan, hydroxypropyl methyl cellulose, hydroxyethyl cellulose, hydroxypropyl cellulose, polyvinyl pyrrolidone, carboxymethyl cellulose, polyvinyl alcohol, sodium alginate, polyethylene glycol, tragacanth gum, guar gum, acacia gum, arabic gum, xanthan gum, polyacrylic acid, methylmethacrylate copolymer, carboxyvinyl polymer, amylose, high amylose starch, hydroxypropylated high amylose starch, dextrin, pectin, chitin, chitosan, levan, elsinan, collagen, inulin, dextran, gelatin, zein, gluten, soy protein isolate, whey protein isolate, casein and mixtures thereof;

a flavor ingredient; and a filler, wherein the filler is one or more of soluble fiber, insoluble fiber, cellulose, sugar, starch, polyhydric alcohol, inorganic material, lubricant, wax, or dyestuff, wherein the dissolvable beverage strip has a thickness of 6.5 to 15 mils and a weight density of approximately 114 mg/in$^2$ to approximately 214 mg/in$^2$, wherein the dissolvable beverage strip fully dissolves in less than or equal to 2 minutes in 8 to 16 ounces of water at a temperature of 10° C.; and wherein the weight ratio of filler to water-soluble polymer is about 0.5 to about 1.4, the weight ratio of filler to flavor ingredient is about 0.8 to about 3.7, and the weight ratio of water-soluble polymer to flavor ingredient is about 0.9 to about 2.7.

2. The dissolvable beverage strip of claim 1 further comprising a humectant.

3. The dissolvable beverage strip of claim 2 wherein the humectant is one or more of glycerin, di-glycerin, propylene glycol, polyethylene glycol, sorbitol, mannitol, ethoxylated monoglyceride, ethoxylated di-glyceride, or triacetin.

4. The dissolvable beverage strip of claim 1 further comprising a sweetener.

5. The dissolvable beverage strip of claim 1 further comprising an emulsifier.

6. The dissolvable beverage strip of claim 5 wherein the emulsifier is one or more of lecithin, mono-glyceride of a fatty acid, di-glyceride of a fatty acid, sorbitan ester, sucrose ester of a fatty acid, propylene glycol ester of a fatty acid, or polysorbate.

7. The dissolvable beverage strip of claim 1 further comprising an active ingredient.

8. The dissolvable beverage strip of claim 7 wherein the active ingredient comprises one or more of a vitamin, an amino acid, an electrolyte replacement, an antioxidant, a stimulant, a sleep enhancer, a botanical ingredient, a probiotic enzyme, a prebiotic, an adaptogen, or a protein.

9. The dissolvable beverage strip of claim 1 further comprising an acidulant wherein the acidulant is one or more of citric acid, malic acid, tartaric acid, or phosphoric acid.

10. A dissolvable beverage strip comprising:

about 0.1% by weight to about 50% by weight water-soluble polymer;

about 0.01% by weight to about 50% by weight flavor ingredient;

about 0.01% by weight to about 50% by weight filler; and wherein the dissolvable beverage strip has a thickness of 6.5 to 15 mils and a weight density of approximately 114 mg/in$^2$ to approximately 214 mg/in$^2$, wherein the dissolvable beverage strip fully dissolves in less than or equal to 2 minutes in 8 to 16 ounces of water at a temperature of 10° C.; and wherein the weight ratio of filler to water-soluble polymer is about 0.5 to about 1.4, the weight ratio of filler to flavor ingredient is about 0.8 to about 3.7, and the weight ratio of water-soluble polymer to flavor ingredient is about 0.9 to about 2.7.

11. The dissolvable beverage strip of claim 10 wherein the water-soluble polymer is one or more of pullulan, hydroxypropyl methyl cellulose, hydroxyethyl cellulose, hydroxypropyl cellulose, polyvinyl pyrrolidone, carboxymethyl cellulose, polyvinyl alcohol, sodium alginate, polyethylene glycol, tragacanth gum, guar gum, acacia gum, arabic gum, xanthan gum, polyacrylic acid, methylmethacrylate copolymer, carboxyvinyl polymer, amylose, high amylose starch, hydroxypropylated high amylose starch, dextrin, pectin, chitin, chitosan, levan, elsinan, collagen, inulin, dextran, gelatin, zein, gluten, soy protein isolate, whey protein isolate, casein and mixtures thereof.

12. The dissolvable beverage strip of claim 10 wherein the filler is one or more of soluble fiber, insoluble fiber, cellulose, sugar, starch, polyhydric alcohol, inorganic material, lubricant, wax, or dyestuff.

13. The dissolvable beverage strip of claim 10 further comprising an acidulant wherein the acidulant is one or more of citric acid, malic acid, tartaric acid, or phosphoric acid.

14. The dissolvable beverage strip of claim 10 further comprising a humectant.

15. The dissolvable beverage strip of claim 14 wherein the humectant is one or more of glycerin, di-glycerin, propylene glycol, polyethylene glycol, sorbitol, mannitol, ethoxylated monoglyceride, ethoxylated di-glyceride, or triacetin.

16. The dissolvable beverage strip of claim 10 further comprising a sweetener.

17. The dissolvable beverage strip of claim 10 further comprising an emulsifier.

18. The dissolvable beverage strip of claim 17 wherein the emulsifier is one or more of lecithin, mono-glyceride of a fatty acid, di-glyceride of a fatty acid, sorbitan ester, sucrose ester of a fatty acid, propylene glycol ester of a fatty acid, or polysorbate.

19. The dissolvable beverage strip of claim 10 further comprising an active ingredient.

20. The dissolvable beverage strip of claim 19 wherein the active ingredient comprises one or more of a vitamin, an amino acid, an electrolyte replacement, an antioxidant, a stimulant, a sleep enhancer, a botanical ingredient, a probiotic enzyme, a prebiotic, an adaptogen, or a protein.

* * * * *